United States Patent
Popescu (10) Patent No.: US 10,182,741 B2
(45) Date of Patent: Jan. 22, 2019

(54) DEVICE FOR POSITIONING AN EXAMINATION OBJECT, METHOD FOR CREATING AN IMAGE WITH THE AID OF AN IMAGING SYSTEM, AND IMAGING SYSTEM

(71) Applicant: Stefan Popescu, Erlangen (DE)

(72) Inventor: Stefan Popescu, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 555 days.

(21) Appl. No.: 14/607,896

(22) Filed: Jan. 28, 2015

(65) Prior Publication Data
US 2015/0208946 A1 Jul. 30, 2015

(30) Foreign Application Priority Data

Jan. 29, 2014 (DE) .................. 10 2014 201 585

(51) Int. Cl.
*A61B 8/00* (2006.01)
*A61B 5/055* (2006.01)
*A61B 5/11* (2006.01)
*A61B 5/00* (2006.01)
*A61B 5/113* (2006.01)
*G01R 33/28* (2006.01)
(Continued)

(52) U.S. Cl.
CPC .......... *A61B 5/0555* (2013.01); *A61B 5/0035* (2013.01); *A61B 5/11* (2013.01); *A61B 5/113* (2013.01); *A61B 5/6892* (2013.01); *A61B 5/721* (2013.01); *A61B 6/0428* (2013.01); *A61B 6/527* (2013.01); *G01R 33/28* (2013.01); *A61B 6/032* (2013.01); *A61B 6/037* (2013.01); *G01R 33/3685* (2013.01); *G01R 33/4814* (2013.01)

(58) Field of Classification Search
CPC .... A61B 5/05; A61B 8/08; A61B 8/00; A61B 8/0883; A61B 8/4245; A61B 8/4416; A61B 8/4477
See application file for complete search history.

(56) References Cited

U.S. PATENT DOCUMENTS 5,400,787 A 3/1995 Marandos
6,684,096 B2 1/2004 Babusis
(Continued)

FOREIGN PATENT DOCUMENTS

DE 102009043532 A1 9/2010

OTHER PUBLICATIONS

Maclaren J. et al., "Prospective Motion Correction in Brain Imaging: A Review"; Magnetic Resonance in Medicine; vol. 69; pp. 621-636; 2013.
(Continued)

*Primary Examiner* — Joel Lamprecht
(74) *Attorney, Agent, or Firm* — Lempia Summerfield Katz LLC (57) ABSTRACT

The embodiments relate to a device for positioning an examination object when using an imaging system. The device includes a positioning device for the purpose of positioning the examination object for data capture by the imaging system, and at least one sensor fixed to the positioning device. The at least one sensor is configured to capture a movement of the examination object relative to the positioning device. The device is configured to provide the movement to the imaging system.

18 Claims, 6 Drawing Sheets

(51) Int. Cl.
  *A61B 6/04* (2006.01)
  *A61B 6/00* (2006.01)
  A61B 6/03 (2006.01)
  G01R 33/36 (2006.01)
  G01R 33/48 (2006.01)

(56) References Cited

U.S. PATENT DOCUMENTS

| | | |
|---|---|---|
| 7,450,985 B2 | 11/2008 | Meloy |
| 7,945,304 B2 | 5/2011 | Feinberg |
| 8,002,706 B2 * | 8/2011 | Vortman ............. A61N 7/02 342/374 |
| 8,374,411 B2 | 2/2013 | Armstrong et al. |
| 8,390,291 B2 | 3/2013 | Briggs |
| 2004/0267111 A1 * | 12/2004 | Feinberg ............. A61B 8/08 600/411 |
| 2005/0171425 A1 | 8/2005 | Burke |

OTHER PUBLICATIONS

Kopeinigg Daniel et al., "Prospective Optical Motion Correction for 3D Time-of-Flight Angiography", Magnetic Resonance in Medicine, vol. 69, pp. 1623-1633, 2013.
Sengupta Saikat et al., "Prospective real time rigid body motion correction at 7 Tesla using inductively coupled wireless NMR markers," Proc. Intl. Soc. Mag. Reson. Med., vol. 21, p. 2578, 2013.
MRI-Pad, Evolve Medical Imaging Group, Evolve Technologies Corporation, p. 1-2 (2013).
German Office Action dated Sep. 29, 2014, for corresponding DE 10 2014 201 585.5, with English Translation.

* cited by examiner

DEVICE FOR POSITIONING AN EXAMINATION OBJECT, METHOD FOR CREATING AN IMAGE WITH THE AID OF AN IMAGING SYSTEM, AND IMAGING SYSTEM

CROSS-REFERENCE TO RELATED APPLICATIONS

This application claims the benefit of DE 10 2014 201 585.5, filed on Jan. 29, 2014, which is hereby incorporated by reference in its entirety.

TECHNICAL FIELD

The present embodiments relate to a device for positioning and/or steadying a living examination object relative to an imaging system, to a method for creating an image of a volume section of the examination object with the aid of the imaging system, and to a correspondingly configured imaging system (e.g., a magnetic resonance installation).

BACKGROUND

When capturing data by an imaging system (e.g., a magnetic resonance installation), movements of the patient continue to represent a serious problem during the data capture, since these movements result in image artifacts. If the movements of the patient are not captured correctly, the data capture is repeated until the artifacts are insignificant enough to allow a satisfactory medical diagnosis on the basis of the images that are created.

In the case of very old patients, sick patients (e.g., patients suspected of having Parkinson's disease), and children in particular, it is almost impossible to prevent movement of the patient. At present, it is often necessary to anesthetize the patient in such cases, in order to restrict the movement of the patient to an acceptable level during the data capture. Anesthetization may represent a life-threatening problem, particularly in the case of very young children.

Physiological movements (e.g., respiration or heartbeat) of the patient may not be prevented. In order to ensure the quality of the data capture in such cases, use is made of motion sensors such as electrocardiogram (ECG) devices or respiration belts, for example. In this case, the problem often arises that these motion sensors are not compatible with the imaging system or may even negatively influence a data capture, e.g., if the motion sensors prevent optimal positioning of magnetic resonance (MR) coils on the chest of the patient.

Data capture using a magnetic resonance installation may sometimes last for 30 to 60 minutes. It is difficult for any patient to remain motionless over such a long period. A flat hard surface of a patient couch is cause for further unease, which is compounded by the restricted space within the magnet and the noise during the data capture, and this adversely then results in numerous movements during the data capture.

SUMMARY AND DESCRIPTION

The scope of the present invention is defined solely by the appended claims and is not affected to any degree by the statements within this summary. The present embodiments may obviate one or more of the drawbacks or limitations in the related art.

An object of the present embodiments is to at least alleviate the problems described above when capturing data by imaging systems.

In certain embodiments, a device is provided for positioning a living examination object while using an imaging system. The device in this case includes a positioning device, in order to position and/or steady the examination object while data is being captured by the imaging system, and sensors that are fixed to the positioning device. The sensors are capable of capturing a movement of the examination object relative to the positioning device. The device is configured to transfer the movement captured by the sensors (e.g., movement information) to the imaging system.

If the device is fixed to the imaging system, or if the spatial relationship between the device and the imaging system is known at all times, a movement of the examination object relative to the imaging system may be computed on the basis of the movement of the examination object as captured by the sensors. Since the sensors are advantageously integrated in the device, it is not necessary to position the sensors if the positioning device is already arranged correctly relative to the examination object. Since the device is capable of forwarding the movement information as captured by the sensors to the imaging system (e.g., in the form of a corresponding signal transfer), compatibility between the sensors and the imaging system is ensured in respect of forwarding the movement information.

The imaging system may include the following systems or installations: (1) a magnetic resonance installation, (2) a computer tomograph, (3) an x-ray system, and (4) a positron emission tomograph.

The sensors may include accelerometers and force sensors by which movements may be captured. In particular, the sensors include one or more ultrasound sensors.

In this embodiment variant, the ultrasound sensor or sensors are securely connected to the positioning device.

In this case, each ultrasound sensor may be configured to capture not only a movement of the examination object relative to the positioning device, but also a movement of an organ within the examination object or a part of the examination object relative to the positioning device and hence relative to the imaging system.

The respective ultrasound sensor may therefore capture, e.g., a movement of the heart of the examination object or a respiration movement of the examination object, such that corresponding movement information may advantageously be reported to the imaging system.

Each ultrasound sensor may include a coaxial cable with a sheath wave trap in this case. The sheath wave trap is configured in this case to attenuate sheath waves that are generated on an external surface of the coaxial cable by the imaging system. Furthermore, each ultrasound sensor may have a low-pass filter by which frequencies above a predefined threshold value (e.g., 50 MHz) are attenuated.

When using the device in connection with a magnetic resonance installation in particular, the sheath wave trap advantageously prevents the occurrence on the external surface of the coaxial cable of any currents that might interfere with the HF pulses generated by the magnetic resonance installation. The low-pass filter also ensures that no currents in a frequency range of the magnetic resonance installation, (e.g., 50 to 500 MHz), occur in the respective ultrasound sensor.

In one embodiment variant, the positioning device includes a support and a holder (e.g., a mattress, a cushion, or a sleeve), wherein the holder is situated on or connected to the support and is itself filled with a fluid or a gel. In this case, the support and the holder are configured to position as statically as possible, and therefore also to steady, the examination object relative to the imaging system with the aid of the holder. In this case, to steady is also understood to provide that the examination object is (e.g., comfortably) accommodated in such a way that only slight movements are to be expected. The sensors are fixed to the support in this case, and arranged or positioned relative to the holder such that an ultrasound wave may propagate from the sensors directly into the gel or the fluid and therefore through the holder.

By virtue of the holder that is filled with the fluid or the gel, the examination object or the patient may be positioned comfortably yet firmly relative to the imaging system. By virtue of the appropriate arrangement of the sensors relative to the holder, it is advantageously unnecessary for the ultrasound waves to pass through a separation layer between various media (e.g., between air and the fluid/gel), which would significantly attenuate the propagation thereof.

The gel or fluid may be selected to be almost invisible in an image of the examination object, which is created by the imaging system. The following variants exist for the fluid or gel for the MR imaging. (1) Water is doped with a paramagnetic compound, so that the water is not visible in MR images. (2) A low-viscosity gelatinous gel is provided. The gel in this case includes approximately 80-93 wt. % water, preservatives, cross-linking substances and antibiotics. The remaining 7-20 wt. % includes substitutes. Another formula includes 0.5-3.0 g $NiSO_4*6H_2O$, and 3.0-7.0 g NaCl for a liter of distilled water. (3) Fluid polymers or liquid plastics are provided, where the polymers or plastics are not visible in MR images, (e.g., as described in U.S. Patent Publication No. 2005/0171425 A1).

According to a further embodiment variant, the device includes one or more local coils that are fixed to the positioning device. Each of these local coils is configured to beam electromagnetic HF waves into the examination object or receive electromagnetic HF waves from the examination object.

By virtue of integrating local coils and sensors within the device, it is advantageously ensured that the local coils and the sensors do not interfere with each other.

The sensors may also include one or more capacitive sensors in addition to or instead of the ultrasound sensors.

The use of capacitive sensors is advantageous in particular if the use of ultrasound sensors causes problems, e.g., if it is not possible to guarantee the unimpeded propagation of the ultrasound waves.

According to a further embodiment variant, the positioning device includes a support (e.g., an examination table) and a holder that is situated thereon or connected thereto. Using the holder (and the support), the examination object may be arranged relative to the imaging system. In this case, a first electrode of the capacitive sensor is arranged in a first region on the support, the first region facing towards the examination object when the examination object is positioned by the positioning device. In particular, the first electrode is arranged on the top side of the examination table, the examination object lying on this top side. A second electrode of the capacitive sensor is attached in a second region on the holder (e.g., the top side of the holder), the second region being in contact with the examination object and in the proximity of the first region when the examination object is positioned by the positioning device.

On the basis of the capacitance of the capacitor that is formed by the two electrodes, the capacitive sensor captures the distance between these two electrodes. If the examination object then moves relative to the support, the distance changes, and this is captured by the change in the capacitance.

In certain embodiments, provision is also made for a method for creating an image of a volume section of a living examination object with the aid of an imaging system. In this case, the method includes the following acts. (1) Imaging data of the volume section is captured with the aid of the imaging system. (2) A movement of the examination object is captured during the capture of the imaging data, with the aid of the device as described above. In particular, the device is either arranged statically relative to the imaging system in this case, or the spatial location of the device relative to the imaging system is known at all times, as applies when using, e.g., an examination table that is introduced into a magnetic resonance installation. (3) The image is created as a function of the imaging data and as a function of the captured movement of the examination object.

The method advantageously utilizes the device, such that movements of the examination object may be captured more precisely and also more easily than is possible according to the prior art. Since the creation of the image takes place on the basis of these precisely captured movements, the quality is also better than what is provided according to the prior art.

Possibilities for creating the image as a function of or with reference to the captured movement of the examination object are as follows: (1) The capture of the imaging data with the aid of the imaging system (in particular, a magnetic resonance installation) is interrupted for as long as a degree of captured movement of the examination object exceeds a first movement threshold value. In other words, when using this variant, imaging data is only captured when the movement of the examination object is slight. (2) The imaging data that is captured within a time period in which a degree of captured movement of the examination object exceeds a second movement threshold value is captured again. In the case of a magnetic resonance installation, for example, that region of the k-space that was captured while the degree of captured movement exceeded the second movement threshold value is captured again. The captured data that was captured while the degree of captured movement exceeded the second movement threshold may then be used or discarded during the reconstruction of the image. (3) The captured movement of the examination object is taken into consideration when creating the image, in order to reproduce every region within the volume section at the correct position in the created image. In other words, when using this variant, the correct position of the corresponding region (e.g., of an organ such as the heart) is determined on the basis of the captured movement (e.g., direction) and is taken into consideration when creating the image.

According to an embodiment variant, operation of the sensors is synchronized with operation of the imaging system. In particular, the sensors are not active during a readout phase of the imaging system, during which the imaging system captures or reads out the imaging data.

In particular, if the imaging system is a magnetic resonance installation and the sensors are ultrasound sensors, no ultrasound waves may be generated or received by the ultrasound sensors if the MR data is being read out following an excitation phase. This advantageously prevents the ultrasound sensors from negatively influencing the readout of the MR data.

Finally, an imaging system is provided that includes a device as described above and is configured to create an image of a volume section of a living examination object. In particular, the device is either arranged statically relative to the imaging system in this case, or the imaging system is configured to be capable of ascertaining the spatial location of said device relative to the imaging system at all times.

Advantages of the imaging system correspond with the advantages of the device, which are described in detail above and therefore need not be repeated here.

In particular, the present embodiments are suitable for the correct capture of imaging data with the aid of an imaging system. The embodiments are not restricted to this field of application since, for example, the device may also capture the movement of a patient when the imaging system is not active. The embodiments may therefore also be used independently of imaging systems, in order to capture or monitor the heartbeat or respiration of a patient, for example.

DETAILED DESCRIPTION

Figure 1:
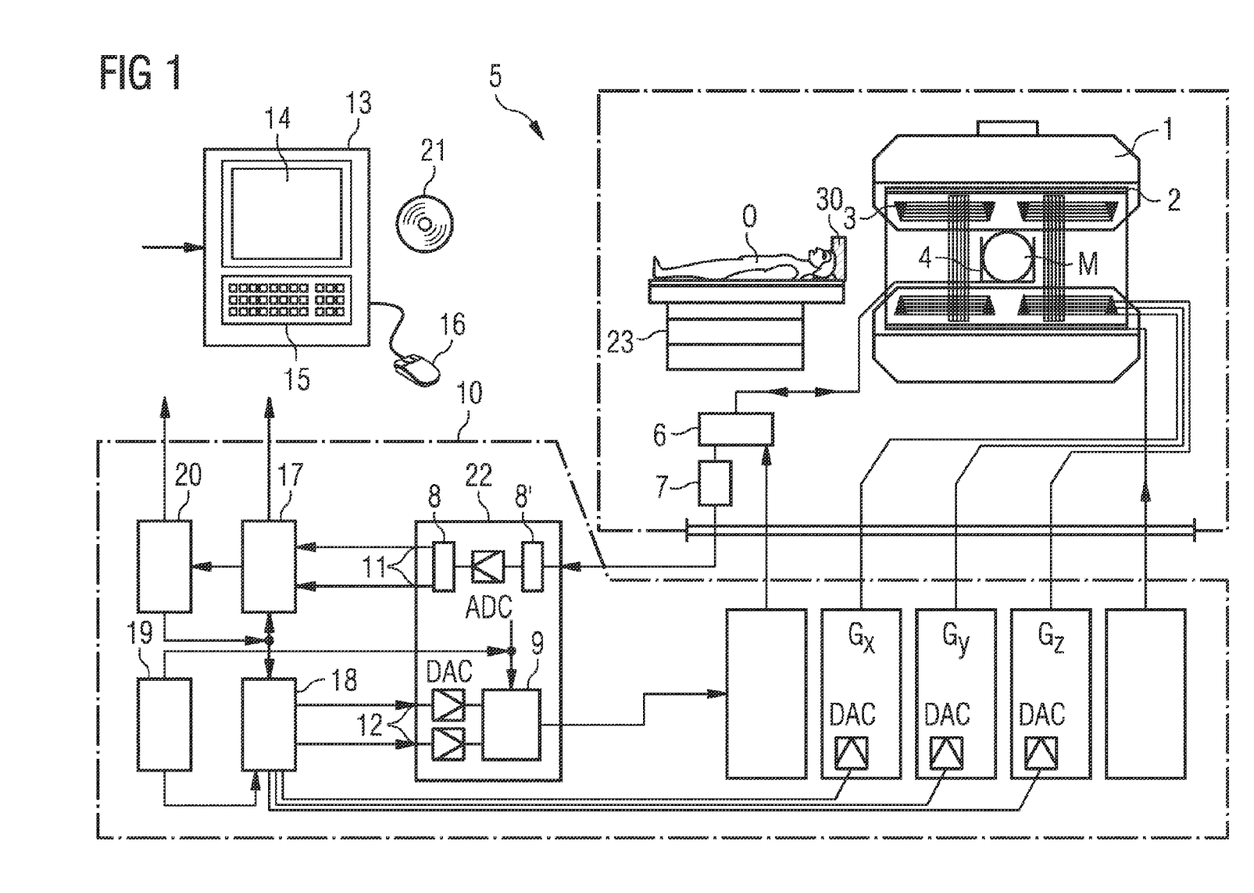
FIG. 1 schematically depicts an embodiment of an imaging system in the form of a magnetic resonance installation.

FIG. 1 depicts a schematic illustration of a magnetic resonance installation 5 (a magnetic resonance imaging device or nuclear spin tomography device). In this case, a basic field magnet 1 generates a temporally constant strong magnetic field in order to polarize or align the nuclear spin in an examination region of an object O, e.g. a human body part that is to be examined, which is lying on a table 23 and is transported steadily into the magnetic resonance installation 5. The high homogeneity of the basic magnetic field, which is required for the measurement of nuclear spin resonance, may be defined in a spherical measuring volume M through which the human body parts to be examined are steadily transported. In order to satisfy the homogeneity requirements and in particular to eliminate temporally invariable influences, so-called shim plates of ferromagnetic material are attached at suitable locations. Temporally variable influences are eliminated by shim coils 2.

A cylindrical gradient field system 3 including three part-windings is used in the basic field magnets 1. Each part-winding is supplied with current by an amplifier in order to generate a linear (and temporally variable) gradient field in the respective direction of the Cartesian system of coordinates. In this case, the first part-winding of the gradient field system 3 generates a gradient $G_x$ in an x-direction, the second part-winding a gradient $G_y$ in a y-direction and the third part-winding a gradient $G_z$ in a z-direction. The amplifier includes a digital-analog converter, which is triggered by a sequence controller 18 in order to ensure the correct timing of the gradient pulse generation.

A high-frequency antenna 4 (or a plurality thereof) is located within the gradient field system 3 and converts the high-frequency pulses emitted by a high-frequency power amplifier into an alternating magnetic field for the purpose of exciting the nuclei and aligning the nuclear spin of the object O to be examined or the region to be examined in said object O. Each high-frequency antenna 4 includes one or more HF transmit coils and one or more HF receive coils in the form of an annular and, for example, linear or matrix arrangement of component coils. The HF receive coils of the respective high-frequency antenna 4 also convert the alternating field originating from the precessional nuclear spin, (e.g., normally the nuclear spin echo signals caused by a pulse sequence of one or more high-frequency pulses and one or more gradient pulses), into a voltage (e.g., measured signal) that is supplied via an amplifier 7 to a high-frequency receive channel 8 of a high-frequency system 22. The high-frequency system 22 that is part of a control device 10 of the magnetic resonance installation 5 further includes a transmit channel 9 in which the high-frequency pulses are generated for excitation of the magnetic nuclear resonance. In this case, the respective high-frequency pulses are represented digitally as a series of complex numbers in the sequence controller 18 on the basis of a pulse sequence that is specified by the installation computer 20. This series of numbers is supplied in the form of a real part and an imaginary part via an input 12 in each case to a digital-analog converter in the high-frequency system 22, and thence to a transmit channel 9. In the transmit channel 9, the pulse sequences are modulated onto a high-frequency carrier signal whose basic frequency corresponds to the resonance frequency of the nuclear spin in the measuring volume.

The changeover from transmit mode to receive mode is effected by a transmit/receive switch 6. The HF transmit coils of the high-frequency antenna(s) 4 beam in the high-frequency pulses in order to excite the nuclear spin in the measuring volume M, and resulting echo signals are sampled via the HF receive coil(s). The nuclear resonance signals thus obtained are demodulated to an intermediate frequency in a phase-sensitive manner in the receive channel 8' (e.g., first demodulator) of the high-frequency system 22, digitized in the analog-digital converter (ADC), and output via the output 11. This signal will subsequently be demodulated to the frequency 0. The demodulation to the frequency 0 and the separation into real and imaginary parts takes place after digitization in the digital domain in a second demodulator 8. A MR image is reconstructed by an image processor 17 from the measured data thus obtained via an output 11. The management of the measured data, the image data and the control programs is performed by the installation computer 20. On the basis of parameters specified by control programs, the sequence controller 18 controls the generation of the desired pulse sequences in each case, and the corresponding sampling of the k-space. In particular, the sequence controller 18 controls the switching of the gradient at the correct time, the emission of the high-frequency pulses with defined phase amplitude, and the receipt of the nuclear resonance signals. The time base for the high-frequency system 22 and the sequence controller 18 is provided by a synthesizer 19. The selection of corresponding control programs for generating an MR image, which are, e.g., stored on a DVD 21, and the display of the generated MR image, is performed via a terminal 13 including a keyboard 15, mouse 16, and display screen 14.

Figure 2:
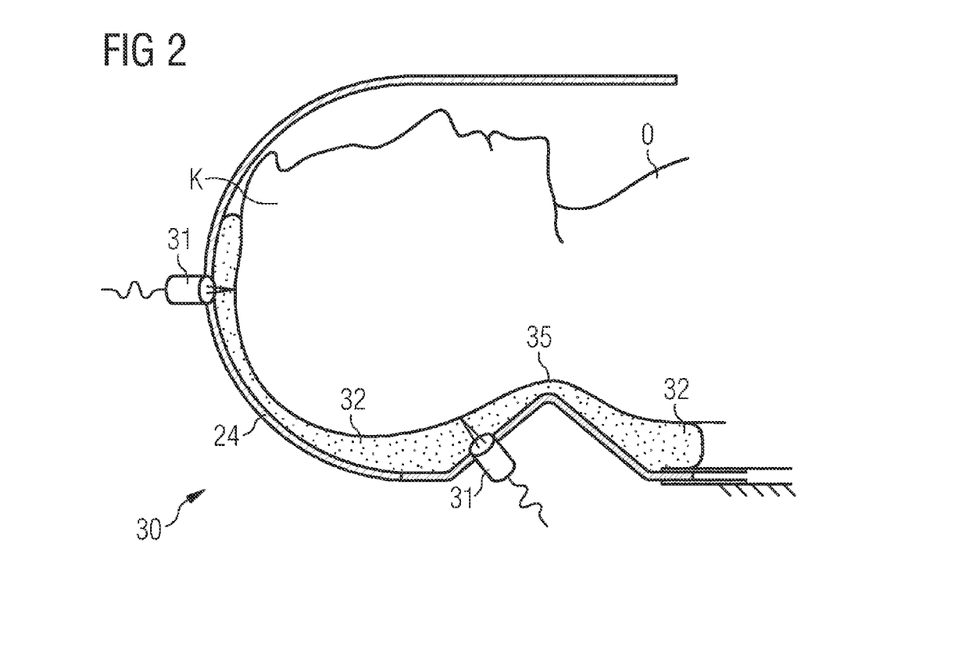
FIG. 2 schematically depicts an embodiment of a device for positioning or steadying a head of a patient.

FIG. 2 schematically illustrates a device 30 for positioning the head K of an examination object O. In this case, the head K is accommodated within a local coil or more precisely on a cushion 35 within a local coil construction 24, wherein the cushion is filled with a fluid or gel 32 and therefore provides a comfortable support for the head. The gel 32 hardly attenuates the propagation of ultrasound waves at all, and moreover has the property of being invisible on MR images, since the gel contains a negligible proportion of water protons. Both the cushion 35 and the local coil construction 24 are component parts of positioning device of the device 30.

A plurality of ultrasound sensors 31 are secured to the positioning device (more precisely to the local coil construction 24) and have a contact area with a low acoustic resistance relative to the fluid or gel 32, such that the transfer of ultrasound waves by the ultrasound sensors 31 into the gel 32 and the receipt of ultrasound waves by the ultrasound sensors from the gel 32 are almost unattenuated.

During the data capture of the magnetic resonance installation, one of the ultrasound sensors 31 in each case is periodically activated in turn in order to emit a short ultrasound wave pulse in each case. All of the ultrasound sensors 31 then operate in receive mode in order to capture echoes that are generated as a result of a reflection of the emitted ultrasound wave pulse at the interface between the head K of the patient O and the positioning device 35, or to capture echoes that originate from the regions within the head K. The present distance between the respective sensor and the examination object O or head K is ascertained as a function of the time period between the emission of the ultrasound wave pulse and the echoes being received at the various ultrasound sensors 31.

Figure 3:
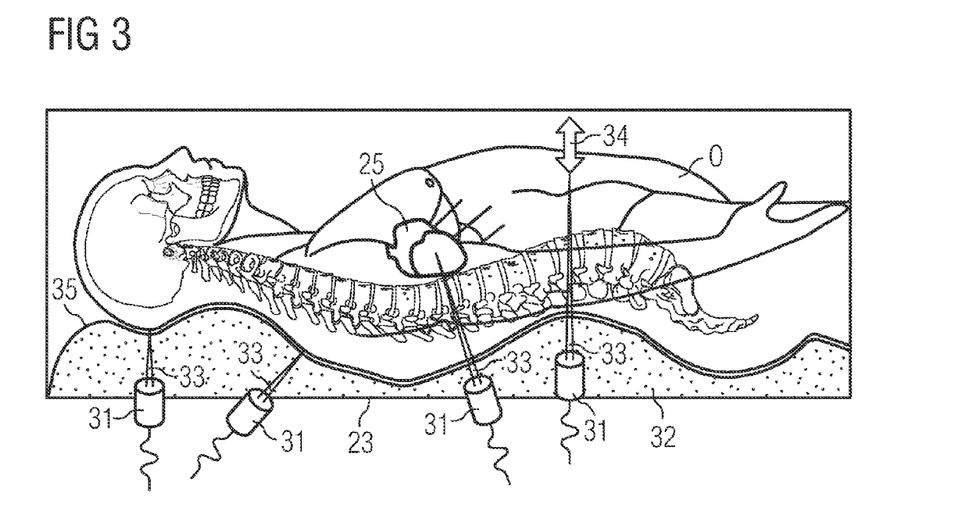
FIG. 3 schematically depicts an embodiment of how movements within the patient are captured.

FIG. 3 depicts a further embodiment variant of a device for positioning an examination object O. The patient O is accommodated in this case on a mattress 35, which is filled with the fluid or gel 32 and arranged on an examination table 23. The gel or fluid 32 may be introduced into the mattress 35 or removed therefrom by a pump, in order to ensure optimal and comfortable positioning of the patient O on the examination table 23. In a similar way to FIG. 2, ultrasound sensors 31 are securely connected to the positioning device, e.g., the examination table 23 in this case. In a similar way to the device 30 illustrated in FIG. 2, one of these ultrasound sensors 31 in each case emits an ultrasound wave 33 (more precisely an ultrasound wave pulse), and all of the ultrasound sensors 31 then capture received echoes of this emitted ultrasound wave 33. The ultrasound sensors 31 are capable of capturing movements of the head, the shoulders, or other external body parts of the patient. In addition to this, the ultrasound sensors 31 are capable of capturing the movement of internal organs (e.g., the movement of the heart 25) or a respiration movement 34 (e.g., on the basis of the movement of the thorax). It is therefore possible to dispense with the respiration belt or even an ECG as routinely used in the prior art, thereby increasing the comfort of the patient O.

Figure 4:
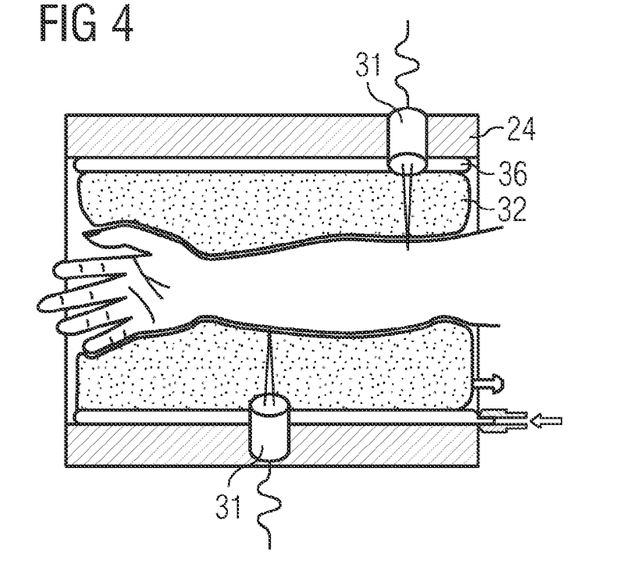
FIG. 4 depicts an embodiment of a positioning device for steadying an arm.

FIG. 4 depicts a further possibility for positioning or accommodating a patient O (just the arm of the patient O in this case). The arm of the patient is held in a sleeve 26, which is arranged within a local coil 24 and filled with a gel 32. As in the case of FIGS. 2 and 3, the ultrasound sensors 31 are secured to the positioning device (the local coil or local coil construction 24 in this case). A similar variant to that illustrated in FIG. 4 exists for positioning or accommodating a knee joint of a patient O.

Figure 5:
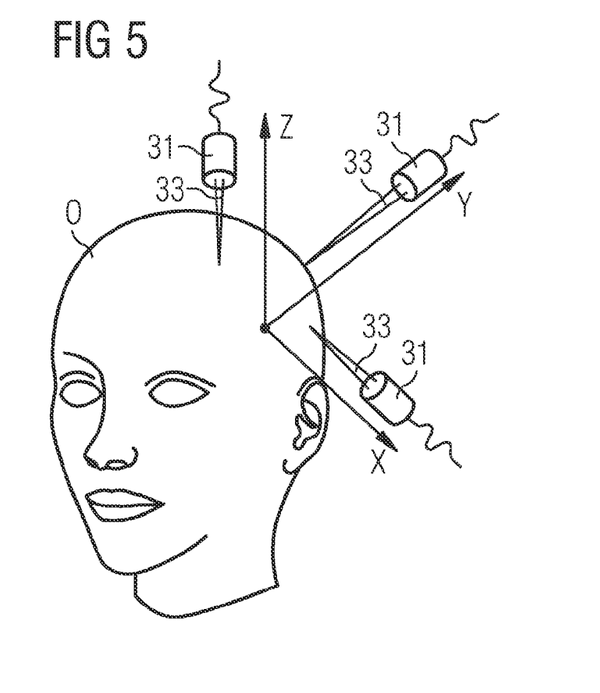
FIG. 5 depicts a principle of capturing movement, including spatial movement direction.
Figure 6:
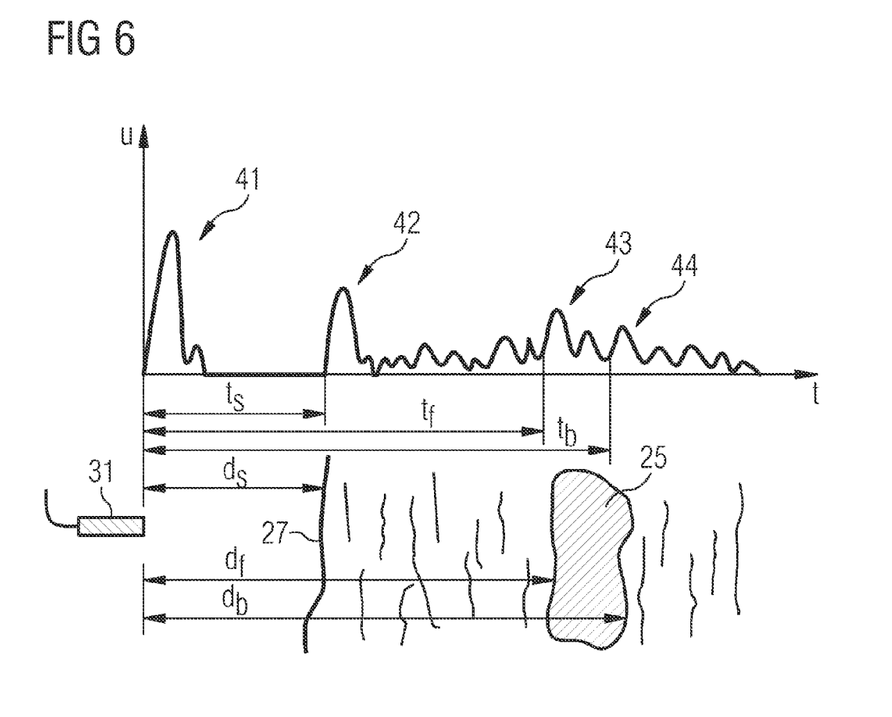
FIG. 6 schematically depicts a principle by which a distance to an object may be captured with reference to reflected ultrasound waves.

FIGS. 5 and 6 are intended to explain the principle of capturing a movement by ultrasound sensors 31.

For example, if three ultrasound sensors 31 are arranged in each case to emit and capture ultrasound waves 33 in directions that are reciprocally perpendicular in each case, as depicted in FIG. 5, each of these three ultrasound sensors 31 may effectively capture a movement component in the corresponding spatial direction X, Y, Z. In combination, these three ultrasound sensors 31 may then capture a movement in any spatial direction.

It is assumed in this case that the propagation speed of an ultrasound wave in the human body is approximately c=1540 m/s. The actual speed in each case may vary slightly from this constant c, depending on the density and elasticity of the respective tissue through which the ultrasound waves travel. In most cases, it is however assumed that the speed of the ultrasound waves through tissue is identical to the speed of the ultrasound waves through liquids such as water, for example.

FIG. 6 depicts the principle by which distances $d_b$, $d_f$, $d_s$ between the respective ultrasound sensor 31 and the patient O (more precisely the outer skin 27 of the patient O) or the anterior surface or posterior surface of an organ 25 may be calculated from a voltage profile (voltage u over the time t) that is generated by an ultrasound sensor 31.

The first maximum 41 in the voltage profile illustrated in FIG. 6 corresponds to the ultrasound wave pulse emitted by the ultrasound sensor 31. Following the emission of this ultrasound wave pulse, the ultrasound sensor 31 operates in a receive mode in which the ultrasound waves received as reflections of the emitted ultrasound wave pulse are converted into a voltage u. The second maximum 42 corresponds to the ultrasound wave that is reflected from the outer skin 27 of the patient O. Since the emitted ultrasound wave pulse also propagates in the body of the patient O, the maximum 43 corresponds to the ultrasound wave reflected from the anterior side of the heart 25, and the maximum 44 to the ultrasound wave reflected from the posterior side of the heart 25.

With reference to the measured time periods $t_b$, $t_f$ and $t_s$ and having knowledge of the propagation speed c of ultrasound waves, it is possible to calculate the distance to the respective object using the following equation (1). In this case, each time period starts with the emission of the ultrasound wave pulse and ends with the receipt of the corresponding echo, and therefore the product of the time period $t_x$ and the propagation speed c is halved in the equation (1):

$$d_x = t_x * c/2 \qquad (1)$$

Figure 7:
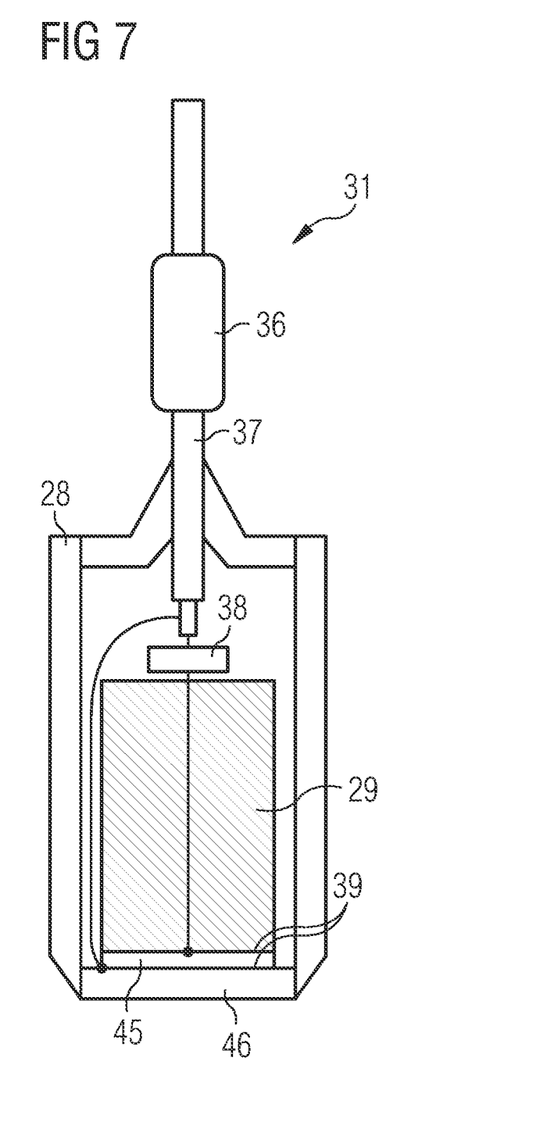
FIG. 7 depicts an embodiment of the basic structure of an ultrasound sensor.

FIG. 7 depicts the structure of an ultrasound sensor 31.

The coaxial cable 37 by which the ultrasound sensor 31 is connected to the control unit of the imaging system includes a sheath wave trap 36. This sheath wave trap 36 makes it possible to prevent HF sheath wave currents, which may occur in a magnetic resonance installation due to emission of HF pulses, for example.

The ultrasound wave sensor 31 also includes an HF filter 38. This filter 38 attenuates frequencies higher than 50 MHz, whereby currents induced by a magnetic resonance installation and lying in a frequency range from 50 to 500 MHz may be filtered out, such that only signals in a frequency range from 1 to 5 MHz are transferred.

Situated within the housing 28 of the ultrasound sensor 31 is a piezoelectric crystal 45, which is connected to two electrodes 39 of the ultrasound sensor 31. Situated above (in FIG. 7) the piezoelectric crystal 45 is a material 29, which absorbs 100% of sound waves. Situated below the piezoelectric crystal 45 is the so-called acoustic window 46, via which ultrasound waves are emitted in transmit mode and received in receive mode.

Figure 8:
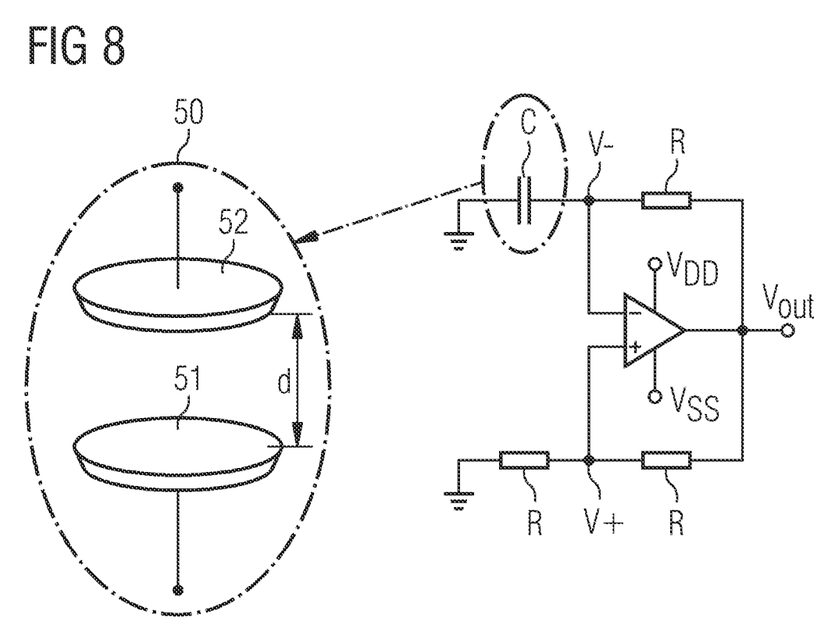
FIG. 8 depicts an embodiment of the basic structure of a capacitive sensor.

FIG. 8 depicts an alternative embodiment variant of a motion sensor in the form of a capacitive sensor 50.

The capacitive sensor 50 includes two electrodes 51, 52. The first electrode 51 is secured to e.g. a support (e.g., to the top side of the examination table 23), while the second electrode 52 is connected to that side of the holder (e.g., the mattress) that is in contact with the patient O or a body part of the patient O. The capacitance C of the capacitor, which is formed by the two electrodes 51, 52, changes with the distance d between the electrodes 51, 52. If the capacitance C that is produced by the capacitive sensor 50 is connected to an RC oscillator circuit as illustrated on the right-hand side of FIG. 8, the output frequency of the output voltage $V_{out}$ is proportional to the distance d between the electrodes 51, 52.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A positioning device for positioning an examination object for data capture by an imaging system, the positioning device comprising:
    an examination table;
    a holder filled with a fluid or gel, wherein the holder is arranged on the examination table and, configured to directly couple the examination object to the examination table;
    sensors fixed to the examination table, wherein the sensors are configured to capture a movement of the examination object relative to the examination table; and
    at least one local coil fixed to the examination table and configured to beam high-frequency waves into the examination object or to receive high-frequency waves from the examination object,
    wherein the examination table and the holder are configured to position the examination object relative to the imaging system by the holder,
    wherein the positioning device is configured to transfer information for the movement of the examination object to the imaging system.

2. The positioning device as claimed in claim 1, wherein the sensors comprise at least one ultrasound sensor.

3. The positioning device as claimed in claim 2, wherein the at least one ultrasound sensor is configured to capture both a movement of the examination object relative to the examination table and a movement of an organ of the examination object relative to the examination table.

4. The positioning device as claimed in claim 3, wherein the at least one ultrasound sensor comprises a coaxial cable with a sheath wave trap for attenuating sheath waves that are generated on an external surface of the coaxial cable by the imaging system, a low-pass filter for attenuating frequencies that are higher than a predefined threshold value, or both the coaxial cable and the low-pass filter.

5. The positioning device as claimed in claim 4, wherein the imaging system comprises a magnetic resonance installation.

6. The positioning device as claimed in claim 5,
    wherein the sensors are arranged relative to the holder such that an ultrasound wave from each sensor may propagate directly into the gel or fluid.

7. The positioning device as claimed in claim 2, wherein the at least one ultrasound sensor comprises a coaxial cable with a sheath wave trap for attenuating sheath waves that are generated on an external surface of the coaxial cable by the imaging system, a low-pass filter for attenuating frequencies that are higher than a predefined threshold value, or both the coaxial cable and the low-pass filter.

8. The positioning device as claimed in claim 1,
    wherein the sensors are arranged relative to the holder such that an ultrasound wave from each sensor may propagate directly into the gel or fluid.

9. The positioning device as claimed in claim 8, wherein the gel or fluid is not visible in an image of the examination object created by the imaging system.

10. The positioning device as claimed in claim 1, wherein the sensors comprise a capacitive sensor.

11. The positioning device as claimed in claim 1, wherein the holder comprises a mattress, a cushion, or a sleeve.

12. The positioning device as claimed in claim 10, wherein the capacitive sensor comprises a first electrode and a second electrode,
    wherein the first electrode is arranged on the examination table in a first region, the first electrode facing towards the examination object when the examination object is positioned by the positioning device, and
    wherein the second electrode may be attached to the holder in a second region, the wherein second electrode is in contact with the examination object and is located in the proximity of the first region when the examination object is positioned by the positioning device.

13. A method for creating an image of a volume section of an examination object using an imaging system, the method comprising:
    positioning the examination object on a surface of a positioning device relative to the imaging system, the positioning device comprising: (1) an examination table; (2) a holder filled with a fluid or gel, wherein the holder is arranged on the examination table and configured to directly couple the examination object to the examination table; (3) sensors fixed to the examination table, wherein the sensors are configured to capture the movement of the examination object relative to the positioning device; and (4) at least one local coil to the examination table and configured to beam high-frequency waves into the examination object or to receive high-frequency waves from the examination object; and
    capturing imaging data of the volume section by the imaging system;
    capturing a movement of the examination object using the sensors of the positioning device while the imaging data is being captured; and
    creating the image based on the imaging data and with reference to the captured movement of the examination object.

14. The method as claimed in claim 13, comprising one or more of the following:
   wherein the capture of the imaging data is interrupted when a degree of captured movement of the examination object exceeds a first movement threshold value,
   wherein the imaging data that is captured within a time period in which a degree of captured movement of the examination object exceeds a second movement threshold value is captured again, or
   wherein the captured movement of the examination object is taken into consideration when creating the image, in order to reproduce a region within the volume section at the correct position in the created image.

15. The method as claimed in claim 14, wherein the sensors are not active during a readout phase of the imaging system, wherein the imaging system reads out the imaging data during the readout phase.

16. The method as claimed in claim 13, wherein the sensors are not active during a readout phase of the imaging system, wherein the imaging system reads out the imaging data during the readout phase.

17. An imaging system comprising:
   a positioning device configured for positioning an examination object for data capture by the imaging system, the positioning device comprising:
   a examination table;
   a holder filled with a fluid or gel, wherein the holder is arranged on the examination table and configured to directly couple the examination object to the examination table;
   sensors fixed to the examination table, wherein the sensors are configured to capture a movement of the examination object relative to the examination table and provide information for the movement of the examination object to the imaging system; and
   at least one local coil fixed to the examination table and configured to beam high-frequency waves into the examination object or to receive high-frequency waves from the examination object, and
   wherein the examination table and the holder are configured to position the examination object relative to the imaging system by the holder, and
   wherein the imaging system is configured to create an image of a volume section of the examination object.

18. The imaging system as claimed in claim 17, wherein the imaging system is configured to:
   capture imaging data of the volume section;
   capture the movement of the examination object with the sensors while the imaging data is being captured; and
   create the image based on the imaging data and with reference to the captured movement of the examination object.

* * * * *